United States Patent
Dale et al.

(10) Patent No.: US 11,185,665 B2
(45) Date of Patent: Nov. 30, 2021

(54) INTRODUCER WITH STEERABLE DISTAL TIP SECTION

(71) Applicant: St. Jude Medical, Cardiology Division, Inc., St. Paul, MN (US)

(72) Inventors: Theodore P. Dale, Corcoran, MN (US); Benjamin E. Morris, Jeffersonville, IN (US); Gregory R. Furnish, Louisville, KY (US); Asela Indaka D. Gunasekara, Louisville, KY (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 295 days.

(21) Appl. No.: 16/379,245

(22) Filed: Apr. 9, 2019

(65) Prior Publication Data
US 2019/0298969 A1    Oct. 3, 2019

Related U.S. Application Data

(62) Division of application No. 15/034,479, filed as application No. PCT/US2014/064918 on Nov. 11, 2014, now Pat. No. 10,293,137.
(Continued)

(51) Int. Cl.
*A61M 25/01*    (2006.01)
*A61F 2/24*    (2006.01)
(Continued)

(52) U.S. Cl.
CPC ... *A61M 25/0113* (2013.01); *A61B 17/00234* (2013.01); *A61B 17/3417* (2013.01);
(Continued)

(58) Field of Classification Search
CPC .......... A61M 25/0062; A61M 25/0147; A61M 25/0138; A61M 25/0136; A61M 25/0133; A61M 25/0054; A61M 25/0013; A61F 2/2427; A61B 2017/00323; A61B 2017/00318; A61B 2017/00309; A61B 2017/003; A61B 17/3417; A61B 17/00234
See application file for complete search history.

(56) References Cited

U.S. PATENT DOCUMENTS 5,354,297 A    10/1994    Avitall
5,381,782 A    1/1995    DeLaRama et al.
(Continued)

FOREIGN PATENT DOCUMENTS

DE    19928272 A1    1/2001
EP    1033144 A1    9/2000
(Continued)

*Primary Examiner* — Jocelin C Tanner
(74) *Attorney, Agent, or Firm* — Dykema Gossett PLLC

(57) ABSTRACT

An introducer with a steerable distal tip section is disclosed. The steerable distal tip section may comprise an articulation support member comprising a laser-cut pattern of symmetrical elongated apertures in which the shape of each aperture is defined by at least three radii, a central radii being the largest and two end radii being smaller. This pattern of apertures can minimize ovaling of the cross-sectional shape of introducer shaft over the length of the deflectable section. The introducer can articulate in multiple planes. A tension pull wire can allow the introducer to resist directional bias.

20 Claims, 16 Drawing Sheets

Related U.S. Application Data

(60) Provisional application No. 61/903,095, filed on Nov. 12, 2013, provisional application No. 61/902,964, filed on Nov. 12, 2013.

(51) Int. Cl.
*A61M 25/00* (2006.01)
*A61M 25/06* (2006.01)
*A61B 17/34* (2006.01)
*A61B 17/00* (2006.01)

(52) U.S. Cl.
CPC ....... *A61F 2/2427* (2013.01); *A61M 25/0013* (2013.01); *A61M 25/0054* (2013.01); *A61M 25/0133* (2013.01); *A61M 25/0136* (2013.01); *A61M 25/0138* (2013.01); *A61M 25/0147* (2013.01); *A61M 25/0662* (2013.01); *A61B 2017/003* (2013.01); *A61B 2017/00309* (2013.01); *A61B 2017/00318* (2013.01); *A61B 2017/00323* (2013.01)

(56) References Cited

U.S. PATENT DOCUMENTS

| | | |
|---|---|---|
| 2006/0135961 A1 | 6/2006 | Rosenman et al. |
| 2008/0300462 A1 | 12/2008 | Intoccia et al. |
| 2009/0192495 A1* | 7/2009 | Ostrovsky ......... A61M 25/0147 604/528 |
| 2010/0069882 A1* | 3/2010 | Jennings ........... A61M 25/0138 604/525 |
| 2010/0145308 A1 | 6/2010 | Layman et al. |
| 2010/0217261 A1* | 8/2010 | Watson ............. A61M 25/0141 606/41 |
| 2012/0203169 A1* | 8/2012 | Tegg ....................... B29C 65/02 604/95.04 |
| 2013/0150831 A1 | 6/2013 | Griffiths |
| 2013/0197306 A1* | 8/2013 | Armand ............ A61B 17/3421 600/109 |
| 2015/0099997 A1 | 4/2015 | Cabiri |

FOREIGN PATENT DOCUMENTS

| | | |
|---|---|---|
| EP | 1457224 A1 | 9/2004 |
| EP | 2489395 A1 | 8/2012 |
| GB | 2478988 A | 9/2011 |
| WO | 93/15790 A1 | 8/1993 |
| WO | 97/33526 A2 | 9/1997 |
| WO | 02/30310 A1 | 4/2002 |
| WO | 2004047899 A1 | 6/2004 |
| WO | 2006065949 A2 | 6/2006 |
| WO | 2012151396 A2 | 11/2012 |

\* cited by examiner

INTRODUCER WITH STEERABLE DISTAL TIP SECTION

CROSS-REFERENCE TO RELATED APPLICATIONS

This application is a division of U.S. application Ser. No. 15/034,479, filed 4 May 2016 (the '479 application), which is a national stage filing based upon international application no. PCT/US2014/064918, filed 11 Nov. 2014 (the '918 application), which claims the benefit of U.S. patent application No. 61/903,095, filed 12 Nov. 2013 (the '095 application) and the '918 application also claims the benefit of U.S. patent application No. 61/902,964, filed 12 Nov. 2013 (the '964 application). The '479 application, the '918 application, the '095 application, and the '964 application are all hereby incorporated by reference in their entirety as though fully set forth herein.

BACKGROUND a. Field

The present disclosure relates generally to introducers used to place catheters and other medical devices at specific locations within the human body. In particular, the present disclosure relates to introducers having a steerable distal tip section.

b. Background

Catheters are used for an ever-growing number of medical procedures. For example, catheters are used for a variety of diagnostic and therapeutic procedures. Typically, a physician manipulates a catheter through a patient's vasculature and to an intended site, such as a site within the patient's heart.

In order to facilitate placement of the catheter at the intended site, it may be introduced through another catheter, commonly known as an "introducer catheter," "introducer," "guide catheter," or "sheath," and these terms may be used interchangeably herein. A modern introducer typically has a high degree of directional control and can therefore be used to place other catheters, which may have little or no directional control, at specific anatomic sites.

Modern introducers are commonly configured with steering or pull wires (also known as puller wires) to control the movement and relative curvature of the device, especially at the distal end. Pull wires typically extend along the length of the introducer from an anchor point (e.g., a pull ring) at or near the distal end of the introducer to a control mechanism at the proximal end of the introducer, such as, for example, a rotatable knob, a plunger, a slider, or a pivot mechanism. Pull wires are used to "pull" on one side or the other side of the introducer to control deflection at the distal end, for example.

The foregoing discussion is intended only to illustrate the present field and should not be taken as a disavowal of claim scope.

SUMMARY

Embodiments of the present disclosure provide an introducer with a steerable distal tip section. The steerable distal tip section may comprise an articulation support member comprising a laser-cut pattern of symmetrical elongated apertures in which the shape of each aperture is defined by at least three radii, a central radii being the largest and two end radii being smaller. This pattern of apertures can minimize ovaling of the cross-sectional shape of introducer shaft over the length of the deflectable section. The introducer can articulate in multiple planes. A tension pull wire can allow the introducer to resist directional bias.

In accordance with an aspect of the present disclosure, a steerable introducer comprises a shaft comprising a proximal end portion and a distal end portion; and a steerable distal tip section attached to the distal end portion of the shaft, the steerable distal tip section comprising an articulation support member comprising a plurality of elongated apertures arranged in a pattern; wherein each pair of adjacent apertures defines a rib therebetween; wherein a shape of each aperture of the plurality of apertures comprises a first arc defining a central section of the aperture, a second arc defining an outboard section of the aperture, and a third arc defining an inboard section of the aperture between the first arc and the second arc; wherein the first arc has a first radius, the second arc has a second radius, and the third arc has a third radius, the first radius being greater than the third radius, and the third radius being greater than the second radius; and wherein, when the introducer is steered to a maximum angle of deflection, and the steerable distal tip section defines a curve portion comprising an inner surface and an outer surface, contact between the ribs is maximized along the inner surface.

In accordance with another aspect of the present disclosure, a steerable introducer comprises a shaft with a proximal end portion, a distal end portion, and a shaft longitudinal axis extending between the proximal end portion and the distal end portion; a steerable distal tip section attached to the distal end portion of the shaft, the steerable distal tip section comprising an articulation support member; a retroflex pull wire extending from the proximal end portion of the shaft to the distal end portion of the shaft, wherein the retroflex pull wire is anchored at a first anchor position on a distal pull ring portion of the articulation support member, the first anchor position being laterally offset from the shaft longitudinal axis in a first direction; at least one tension pull wire extending from the proximal end portion of the shaft to the distal end portion of the shaft, wherein the at least one tension pull wire is anchored at a second anchor position on a proximal pull ring portion of the articulation support member, the second anchor position being (i) laterally offset from the shaft longitudinal axis in a second direction and (ii) angularly offset from the distal pull ring portion by a first angle, wherein the first direction is different from the second direction, and wherein the first angle is about 180 degrees; wherein tension on the retroflex pull wire causes the steerable distal tip section to bend in the first direction; and wherein the tension on the tension pull wire opposes shaft bending in the first direction.

In accordance with another aspect of the present disclosure, a steerable introducer comprises a shaft with a proximal end portion, a distal end portion, and a shaft longitudinal axis extending between the proximal end portion and the distal end portion; a steerable distal tip section attached to the distal end portion of the shaft, the steerable distal tip section comprising an articulation support member; a first pull wire extending from the proximal end portion of the shaft to the distal end portion of the shaft, wherein the first pull wire is anchored at a first anchor position on the articulation support member, the first anchor position being laterally offset from the shaft longitudinal axis in a first direction; a second pull wire extending from the proximal end portion of the shaft to the distal end portion of the shaft, wherein the second pull wire is anchored at a second anchor position on the articulation support member, the second anchor position being (i) laterally offset from the shaft longitudinal axis in a second direction and (ii) angularly offset from the first anchor position by a specified angle, wherein the first direction is different from the second direction; wherein tension on the first pull wire causes the introducer to bend in the first direction; and wherein the tension on the second pull wire causes the introducer to bend in the second direction.

The foregoing and other aspects, features, details, utilities, and advantages of the present disclosure will be apparent from reading the following description and claims, and from reviewing the accompanying drawings.

DETAILED DESCRIPTION

In the field of cardiovascular surgery, introducer catheters can be used to navigate through the patient's vasculature such that a valve repair device can be properly positioned to repair a malfunctioning cardiac valve, for example. Limitations presented by many prior introducers include ovaling of the introducer's cross-sectional shape (taken perpendicular to the introducer's longitudinal axis) upon deflection, being unable to articulate in multiple planes, and exhibiting directional bias when pull wires are used to steer the introducer. Embodiments of the present disclosure describe steerable introducer catheters in which the above limitations have been minimized or eliminated.

Figure 1:
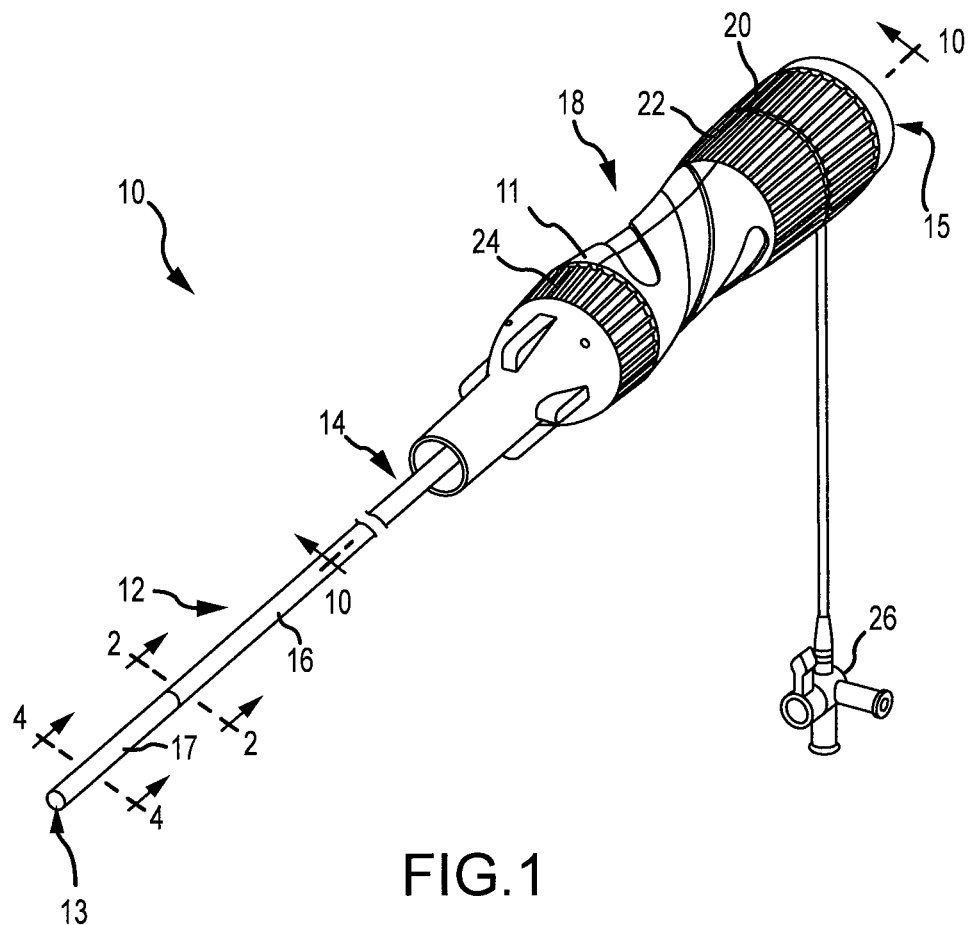
FIG. 1 is an isometric view of an exemplary embodiment of an introducer in accordance with the present teachings.

Referring now to the figures, in which like reference numbers refer to the same or similar features in the various views, FIG. 1 illustrates one exemplary embodiment of a steerable introducer 10 comprising a shaft 16 having a distal end portion 12 and a proximal end portion 14. The introducer shaft 16 may include a steerable distal tip section 17 connected at its distal end portion 12. The proximal end portion 14 of the introducer shaft 16 can be operably connected to a handle assembly 18, which assists in guiding or steering the introducer shaft 16 during medical procedures. The handle assembly 18 may include operational actuators or knobs, such as a tension knob 20, an articulation knob 22, and a side steering knob 24, which may be rotatable with respect to a handle body 11. Alternatively, such actuators may be longitudinally movable, pivotable, rockable, or otherwise movable with respect to a handle body and/or an introducer shaft. As will be discussed in more detail below, such relative movement may cause the steerable distal tip section 17 to deflect, bend, steer, and/or articulate.

The introducer 10 may also include a section of side-port tubing with a stopcock 26 at its free end. In the configuration shown in FIG. 1, the connected end of the side-port tubing is connected to the handle assembly 18 near the proximal end of the handle assembly 18. The stopcock valve and side-port tubing facilitates, for example, the introduction of saline to flush the introducer before or during use in a patient, or the introduction of contrast media or drugs into the lumen of the introducer shaft 16. The handle assembly may also include a hemostasis valve (not shown) in the longitudinal, proximal end 15 of the handle assembly 18 to facilitate access to the lumen 34 (discussed below in connection with FIG. 2) of the introducer 10 while minimizing blood loss and to enable the introduction of catheters and other tool into the lumen of the introducer shaft 16 and out a distal end 13 of the shaft.

Figure 2:
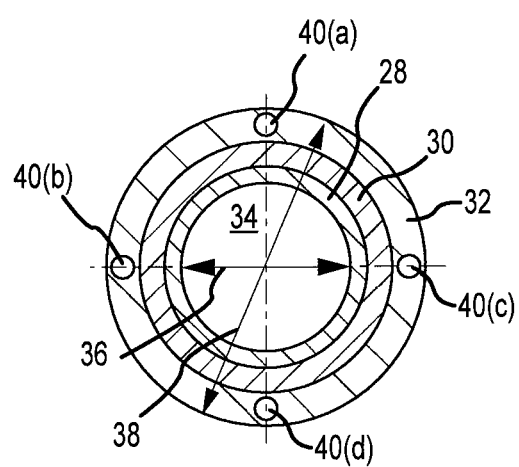
FIG. 2 is a cross-sectional view of the introducer taken along line 2-2 of FIG. 1, revealing additional details about an exemplary shaft construction.

FIG. 2 depicts a cross-sectional view of an exemplary embodiment of the introducer shaft 16 taken along line 2-2 of FIG. 1. The shaft 16 comprises a tubular polymeric inner liner 28, a braided torque-transfer layer 30, and an outer layer 32 formed of a single polymeric material or a combination of different materials. Outer layer 32 can be formed from polymer tubes comprised of polyether block amides (e.g., Pebax®), polytetrafluoroethylene (PTFE), or etched PTFE, for example. The inner liner 28 defines a major lumen 34 with an inner diameter 36. In an exemplary embodiment, the inner diameter 36 may be about 12 French. In such an embodiment, an outer diameter 38, defined by outer layer 32, can be about 14 French, for example. Additionally, the outer layer 32 can further include one or more minor lumens 40(a)-(d). Minor lumens 40(a)-(d) can be adapted to receive a pull wires 46(a)-(d), respectively, designed to steer, articulate, deflect, and/or straighten shaft 16. Pull wires 46(a)-(d) will be discussed in greater detail below.

Figure 3A:
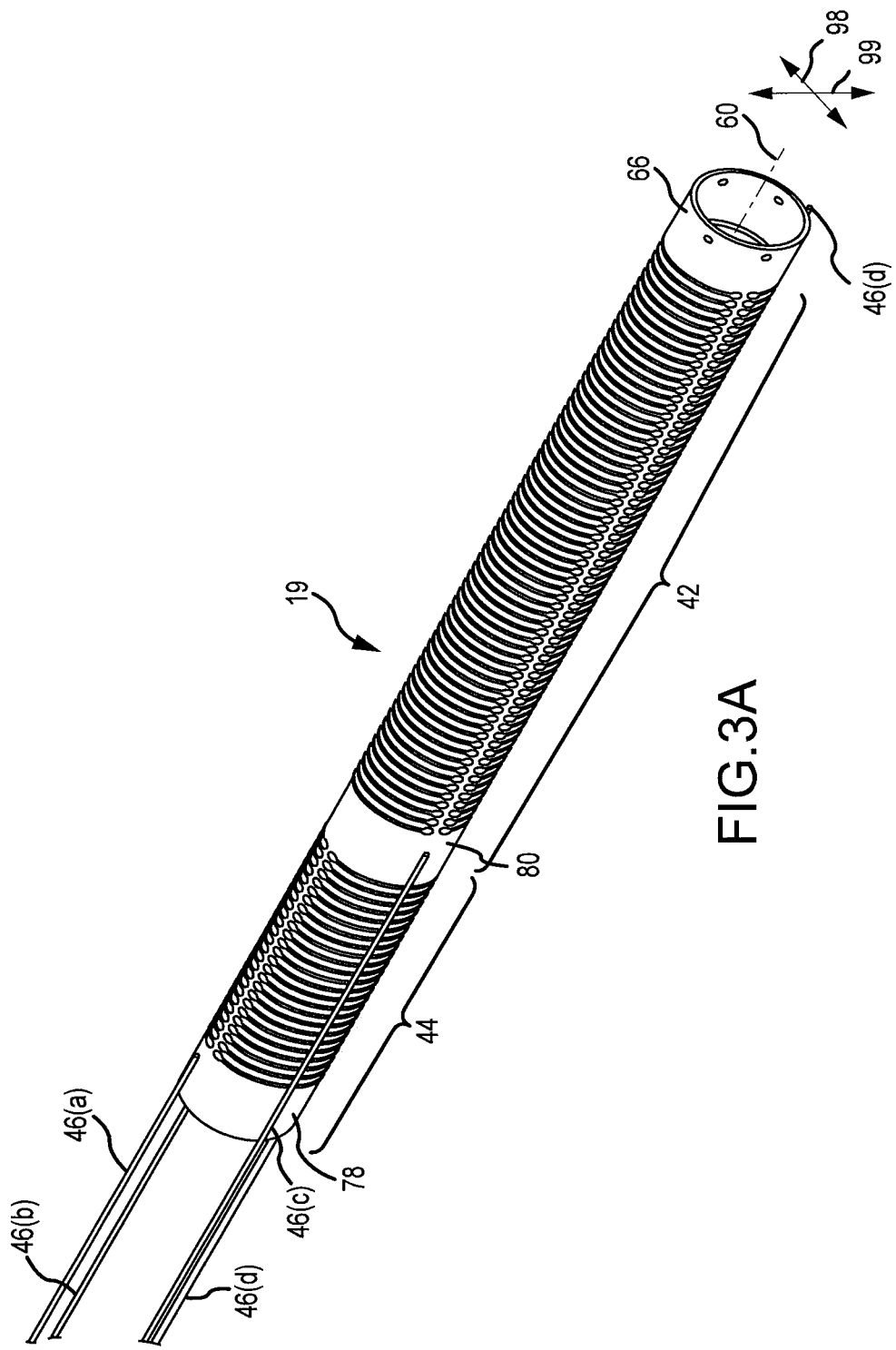
FIG. 3A is an isometric view of components comprising a portion of a steerable distal tip section of an introducer, depicting a plurality of pull wires operatively connected to a bi-planar articulation support member.

FIG. 3A is an isometric view of components comprising a portion of a steerable distal tip section 17 of an introducer 10, depicting a plurality of pull wires 46(a), 46(b), 46(c), 46(d) operatively connected to a bi-planar strut or articulation support member 19. In an exemplary embodiment, the articulation support member 19 is constructed of a stainless steel tube with a laser-cut pattern defined therein. The laser-cut pattern, which is described in more detail below with respect to FIGS. 4A and 4B, is designed to facilitate deflection of the steerable distal tip section 17 while minimizing ovaling of the introducer's cross-sectional shape taken perpendicular to the introducer's longitudinal axis. The laser-cut pattern can be oriented differently in different portions of the articulation support member 19 to allow multiple planes or directions of deflection to be achieved. In FIG. 3A, region 42 can be deflectable up-and-down from −20 to 120 degrees in the direction of arrow 99, for example, and region 44 can be deflectable left-and-right up to 30 degrees (e.g., 15 degrees in each direction) in the direction of arrow 98. In other embodiments, the multiple planes in which deflection occurs are not necessarily 90 degrees apart; instead, they can be 60 or 30 degrees apart, for example, to facilitate maneuvering of the introducer within any particular anatomic structure.

Figure 4:
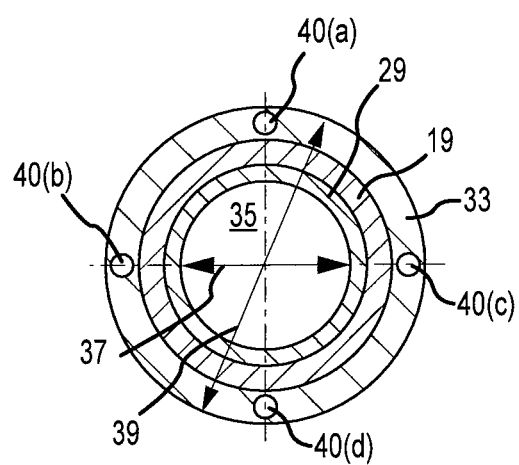
FIG. 4 depicts a cross-sectional view of an exemplary embodiment of the steerable distal tip section 17 taken along line 4-4 of FIG. 1.

FIG. 4 depicts a cross-sectional view of an exemplary embodiment of the steerable distal tip section 17 taken along line 4-4 of FIG. 1. The steerable distal tip section 17 comprises a tubular polymeric inner liner 29, articulation support member 19 formed of stainless steel or other materials, and an outer layer 33 formed of a single polymeric material or a combination of different materials. The materials that form the articulation support member can be highly visible under fluoroscopy as well as contrast-enhanced echogenic ultrasound. Outer layer 33 can be formed from polymer tubes comprised of polyether block amides (e.g., Pebax®), polytetrafluoroethylene (PTFE), or etched PTFE, for example. The inner liner 29 defines a major lumen 35 with an inner diameter 37. In an exemplary embodiment, the inner diameter 37 may be about 12 French. In such an embodiment, an outer diameter 39, defined by outer layer 33, can be about 14 French, for example. Additionally, the outer layer 33 can further include one or more of the minor lumens 40(a)-(d), adapted to receive pull wires 46(a)-(d), respectively, as discussed below.

Figure 3B:
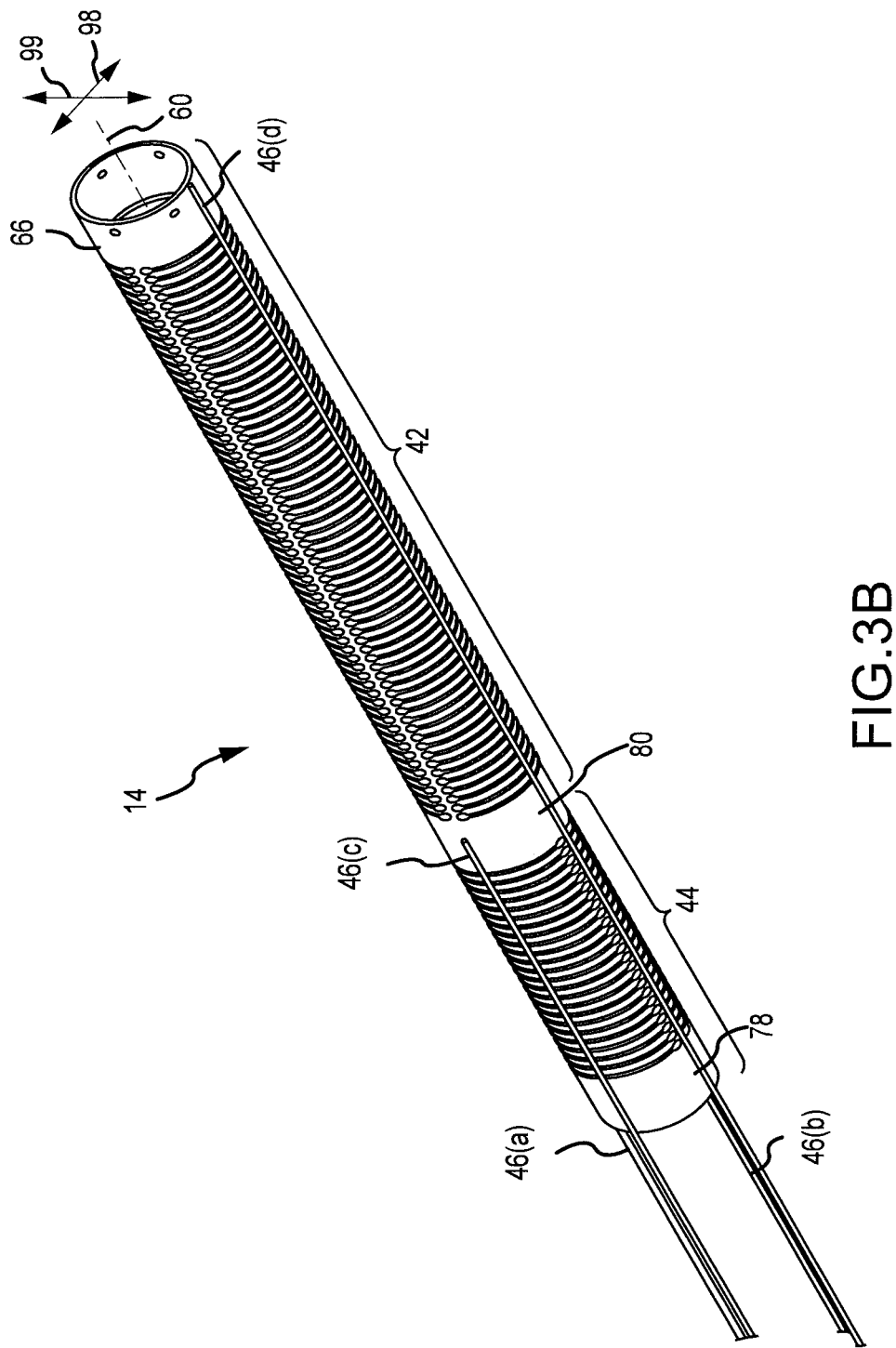
FIG. 3B is another isometric view of the steerable distal tip section of an introducer shown in FIG. 3A.
Figure 5A:
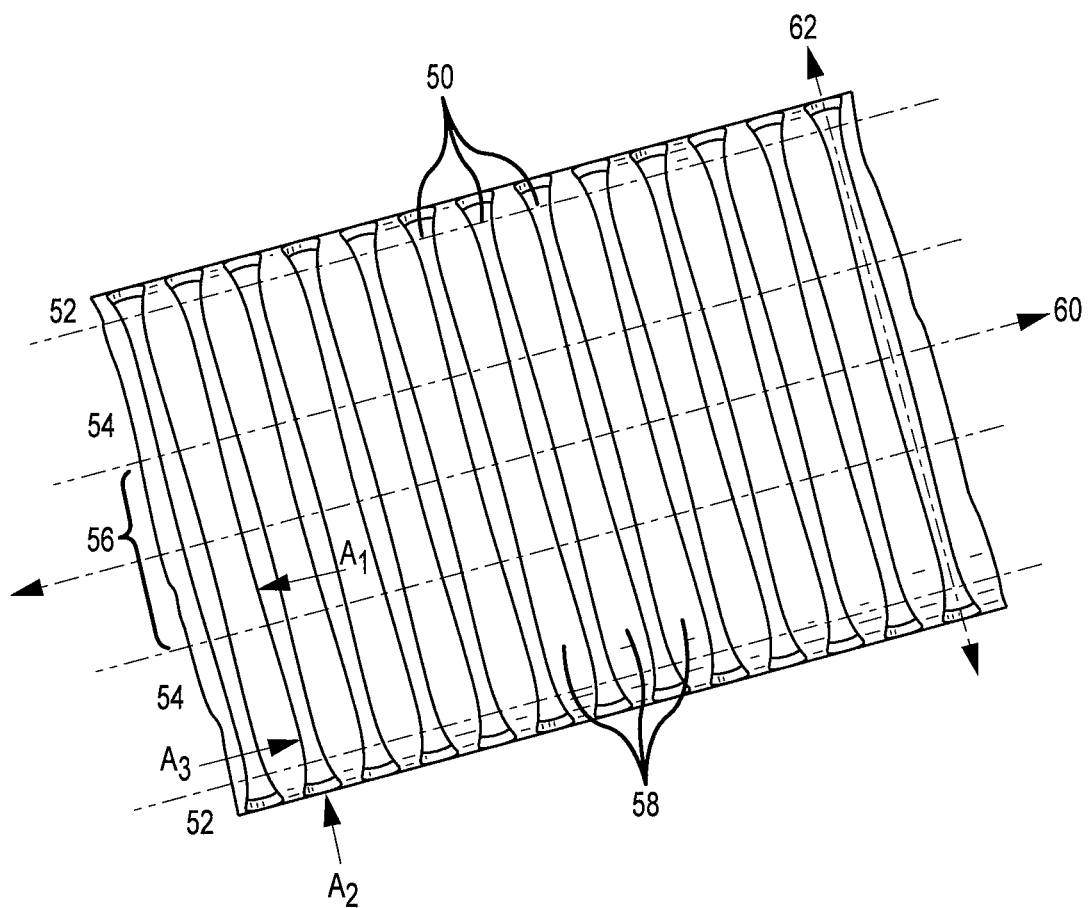
FIG. 5A is an enlarged, fragmentary view of a portion of an articulation support member, showing details of a laser-cut pattern of apertures.

FIG. 5A is an enlarged, fragmentary view of a section of the articulation support member 19 comprising part of the steerable distal tip section 17, and shows details of one embodiment of a laser-cut pattern. In this embodiment, each aperture 50 extends about 180 degrees around the surface of the articulation support member 19, substantially symmetrically about an imaginary plane (such a plane would contain, for example, axis 62 shown in FIGS. 5A and 5B) that is perpendicular to the longitudinal axis 60 of the articulation support member 19 (see FIG. 3). This can also be seen to good advantage in FIGS. 6A and 6B described below. In the depicted embodiment, the shape of each aperture 50 can be described according to the curvature of different sections of the aperture 50. The apertures 50 can be symmetrical about both longitudinal axis 60 and transverse axis 62 (substantially perpendicular to the longitudinal axis 60). In the example shown in FIGS. 5A and 5B, three different arcs—A1, A2, and A3—form the shape of the aperture 50.

Arcs A1, A2, and A3 each have a corresponding radius (not shown). Thus, the shape of the aperture 50 can be described in terms of the three radii, R1, R2, and R3. In other embodiments, the shape of each aperture 50 can include five, seven, or more arcs and corresponding radii. Looking at the aperture 50 lengthwise (e.g., left-to-right in FIG. 4B), the aperture may be thought of as comprising five sections, 52, 54, 56, 54', 52', wherein, since the aperture is symmetrical in this embodiment about axis 60, the two outboard sections 52, 52' are mirror images of each other, and the two inboard sections 54, 54' are mirror images of each other. Each end of the overall aperture 50 comprises part of outboard sections 52, 52' and has an arc A2 with radius R2. The central portion of aperture 50, shown in section 56, has an arc A1 with radius R1. Further, both inboard sections 54, 54' have an arc A3 with radius R3. In this example, R1 is greater than R3, and R3 is greater than R2. A2 provides generous strain relief during flexion of steerable distal tip section 17. A3 provides a boundary surface as the opposing aperture surfaces come together during compressive loading. A1 is a continuation between arc A3 and its symmetric twin on the opposing side of axis 60. In an exemplary embodiment, R1 is about 1-3 inches, or about 2.2821 inches; R2 is about 0.002-0.009 inches, or about 0.0065 inches; and R3 is about 0.1-0.5 inches, or about 0.3238 inches.

Figure 5B:
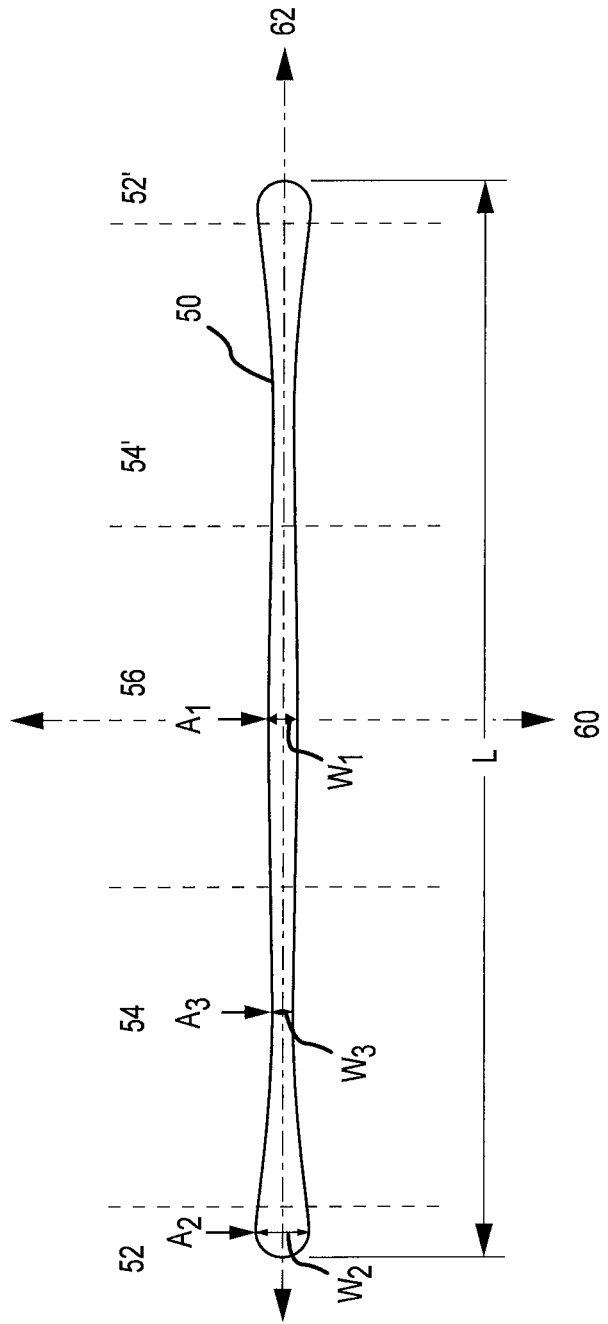
FIG. 5B is an enlarged, flattened view of a single aperture of the plurality of apertures depicted in FIG. 5A.

FIG. 5B shows a single aperture 50 as it would appear if it were laid flat (rather than on a cylindrical body, as it actually is). In an exemplary embodiment, the width W1 of aperture 50 in section 56 is about 0.00805 inches at the widest point; the width W2 of aperture 50 in sections 52, 52' is about 0.013 inches at the widest point; and the width W3 of aperture 50 in sections 54, 54' is about 0.00597 inches at the widest point. Additionally, in this embodiment, aperture 50 has a length L of 0.27025 inches.

Figure 6A:
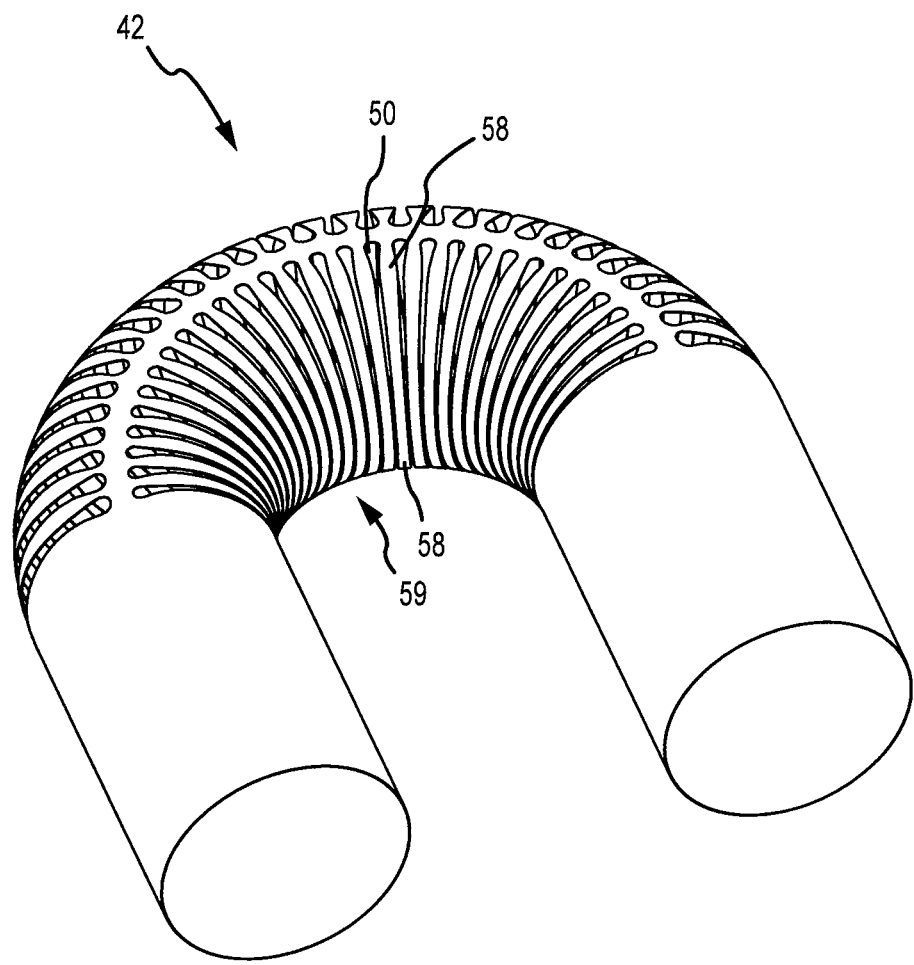
FIG. 6A is a schematic, isometric view of a fully-deflected articulation support member according to an embodiment.
Figure 6B:
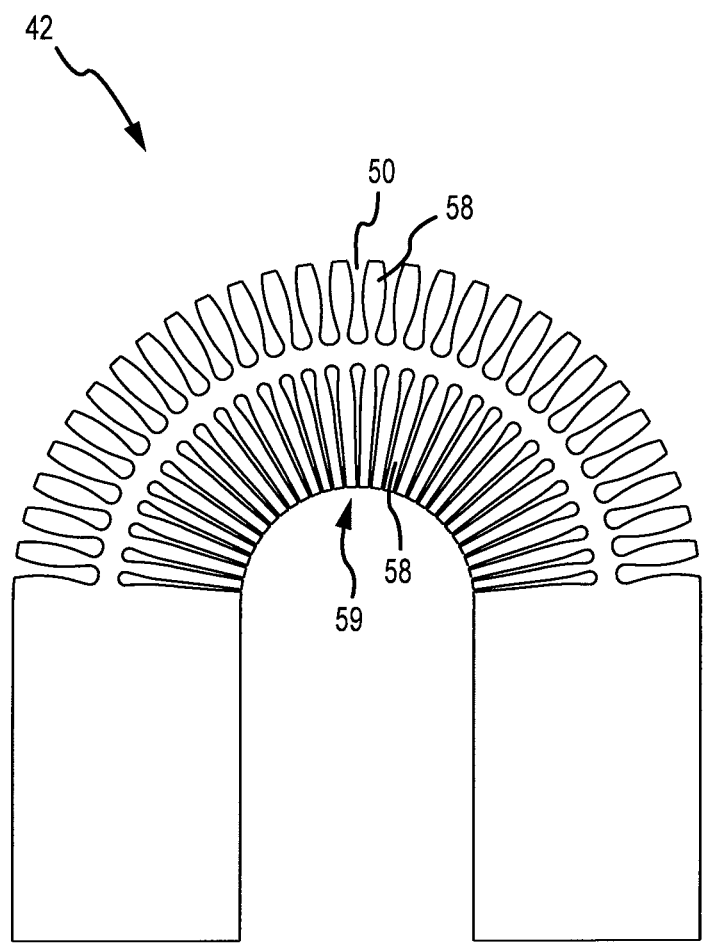
FIG. 6B is a schematic plan view of the fully-deflected articulation support member that is also shown in FIG. 6A, showing, for example, that the articulation support member retains its substantially circular cross section even when fully deflected.

As shown in FIGS. 6A and 6B, the shape of aperture 50 is designed such that, as a region of the articulation support member 19 (e.g., region 42 shown in FIGS. 6A and 6B) is deflected toward the shape depicted in FIGS. 6A and 6B, the apertures 50 begin to close as adjacent ribs 58 of the articulation support member 19 approach each other and start to become substantially parallel to each other along the inner surface 59 of the articulation support member 19. In the examples shown in FIGS. 6A and 6B, when the steerable distal tip section 17 is fully deflected, the edges of adjacent ribs 58 abut each other in region 56 along the inner surface 59 of the articulation support member 19. Thus, the laser-cut design of the articulation support member 19 can minimize or prevent "pinch points" (i.e., short sections of relatively high contact pressure) from being created between adjacent ribs 58 during deflection. Furthermore, the presently described design can minimize or prevent ovaling or other undesirable changes in the cross-sectional shape of the steerable distal tip section 17 during deflection.

In an exemplary embodiment, the minimum deflection radius of steerable distal tip section 17 (FIG. 1) is proportional to the width W1 of the apertures (FIG. 5B) multiplied by the number of apertures for a given distance away from the longitudinal axis 60 (FIG. 3), given a uniform pattern of apertures. The deflection angle is driven by the number of apertures over a given length of the steerable distal tip section 17. A small number of uniform apertures over a short length of steerable distal tip section 17 will yield a small deflection angle, while a larger number of uniform apertures over a longer length of steerable distal tip section 17 will yield a larger deflection angle.

Non-uniform apertures may be employed as well to achieve various desired deflection shapes. For example, a pattern in which the aperture width W1 at the most proximal end of the steerable distal tip section 17 is proportionately small, gradually increases towards the center region of the steerable distal tip section 17, and then gradually decreases in a mirror fashion from the center to the distal end of the steerable distal tip section 17, can result in a sinusoidal curvature. Another example is an aperture pattern that follows a helix along the length of the steerable distal tip section 17. When compressed by force applied through a pull wire, the distal end of the steerable distal tip section 17 would deflect in a similar helical/"cork screw" manner.

Figure 7A:
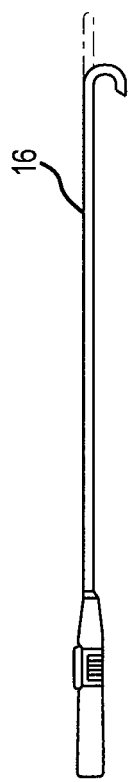
FIG. 7A is a side view of an introducer exhibiting desired articulation from a substantially straight configuration (phantom lines) to a fully-deflected configuration (solid lines).
Figure 7B:
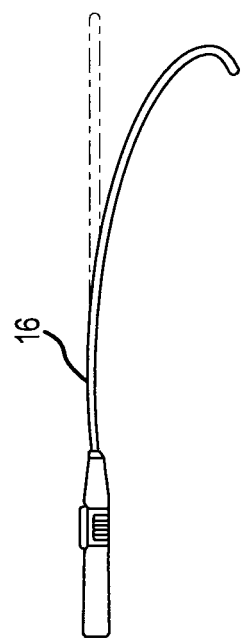
FIG. 7B is similar to FIG. 7A, but depicts a side view of an introducer exhibiting bias upon articulation.

Referring now to FIGS. 7A and 7B, an articulation of introducer shaft 16 is shown. FIG. 7A illustrates the correct, desired articulation of shaft 16, whereas FIG. 7B illustrates the bias in shaft 16 that is typically observed upon articulation. This bias can be due to, for example, inadequate flexibility or strength of shaft 16 under compressive loading. In order to retard or minimize such bias, a tension pull wire may be employed.

Referring back to FIG. 3A, pull wire 46(*a*) is an example of a tension pull wire designed to oppose bending bias caused by retroflex pull wire 46(*d*). Tension pull wire 46(*a*) can cause deflection of the shaft 16 up to about 20 degrees, while retroflex pull wire 46(*d*) can cause deflection of the steerable distal tip section 17 from 0 to about 120 degrees. In this example, one tension pull wire 46(*a*) is shown, but in other examples more than one tension pull wire 46(*a*) may be present. In at least one embodiment, a second tension pull wire may be positioned proximate the tension pull wire 46(*a*) shown in FIG. 3A. Also shown in FIG. 3A are left side steering pull wire 46(*b*) and right side steering pull wire 46(*c*). In the illustrated embodiment, retroflex pull wire 46(*d*) is offset from tension pull wire 46(*a*) by about 180 degrees. Also, retroflex pull wire 46(*d*) is laterally offset from the longitudinal axis of the introducer shaft 16 in one direction, and tension pull wire 46(*a*) is laterally offset from the longitudinal axis of the introducer shaft 16 in the opposite direction. The pull wires 46 can be attached at the proximal end portion 14 of shaft 16 (see FIG. 1). Tension pull wire 46(*a*) can be attached (e.g., via laser welding, adhesive material, mechanical means such as wrapping, torturous path, or tying, or other mechanisms of attachment) at a proximal pull ring portion 78 of articulation support member 19. Left side steering pull wire 46(*b*) and right side steering pull wire 46(*c*) can be attached at an intermediate pull ring portion 80 of articulation support member 19. Retroflex pull wire 46(*d*) can be attached at a distal pull ring portion 66 of articulation support member 19, as shown to good advantage in FIG. 3B.

Figure 8:
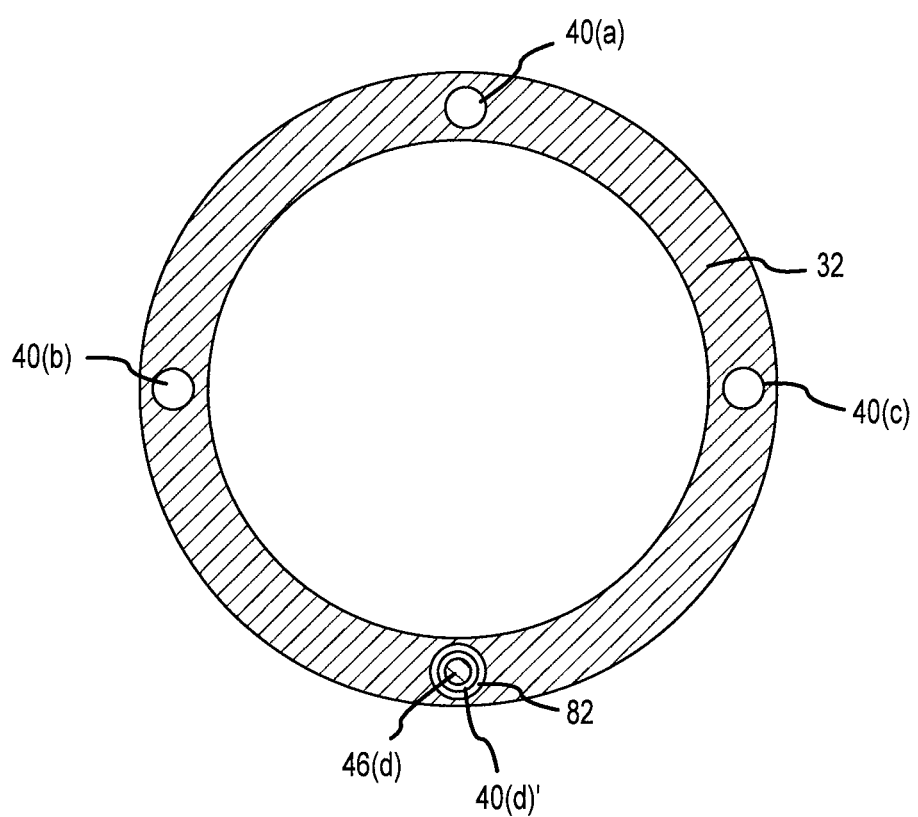
FIG. 8 is a cross-sectional view of an introducer similar to that shown in FIG. 2.

FIG. 8 is a cross-sectional view of the shaft 16 taken along line 2-2 of FIG. 1, showing only the outer layer 32. In an embodiment, retroflex pull wire 46(*d*) (within a minor lumen 40(*d*)') can be located within the outer layer 32 of the shaft 16 portion of the introducer 10, as shown in FIG. 7. Furthermore, retroflex pull wire 46(*d*) can be lined with PTFE and a stainless steel lining 82 (e.g., a tube or coil) to enhance torque transfer and to ensure device integrity. The stainless steel lining 82 may be used to provide a smoother lumen for the retroflex pull wire 46(*d*) and allow it to move more freely within the lumen. In another embodiment, one or more of tension pull wire 46(*a*), left side steering pull wire 46(*b*), and right side steering pull wire 46(*c*) (see FIG. 3) can also be lined with a stainless steel lining that may be similar or identical to lining 82.

Figure 9:
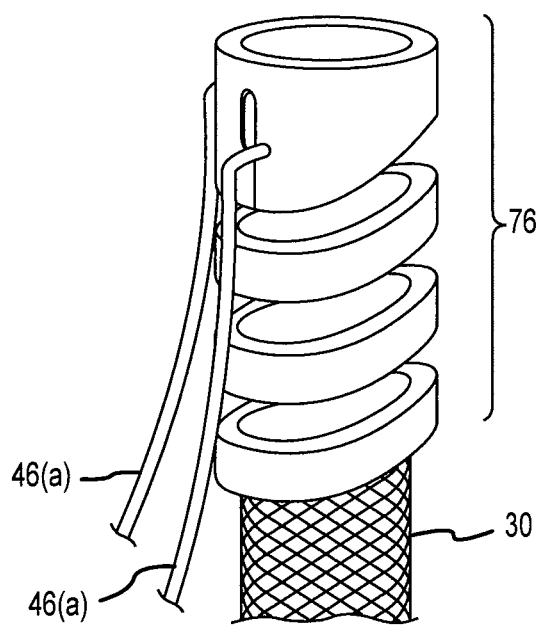
FIG. 9 is an isometric view of an alternative anchor region for tension pull wires, shown attached at a distal end of an introducer shaft.

FIG. 9 is a an isometric view of an alternative anchor region 76 for tension pull wires 46(*a*). Anchor region 76 is shown attached to braided torque-transfer layer 30 (see FIG. 2) at the distal end of shaft 16 (see FIG. 1). In this embodiment, tension pull wires 46(*a*) are attached at anchor region 76 rather than at the proximal pull ring portion 78 of articulation support member 19. Articulation support member 19 (not shown in FIG. 9) can attach (e.g., via laser welding, adhesive material, mechanical means such as wrapping, torturous path, or tying, or other mechanisms of attachment) to the distal end of anchor region 76. Anchor region 76 can be constructed of stainless steel tube with a helical laser-cut pattern as shown and/or include other features, such as through-holes, to secure the shaft 16 and provide strain relief where braided torque-transfer layer 30 terminates and attaches to anchor region 76.

Figure 10:
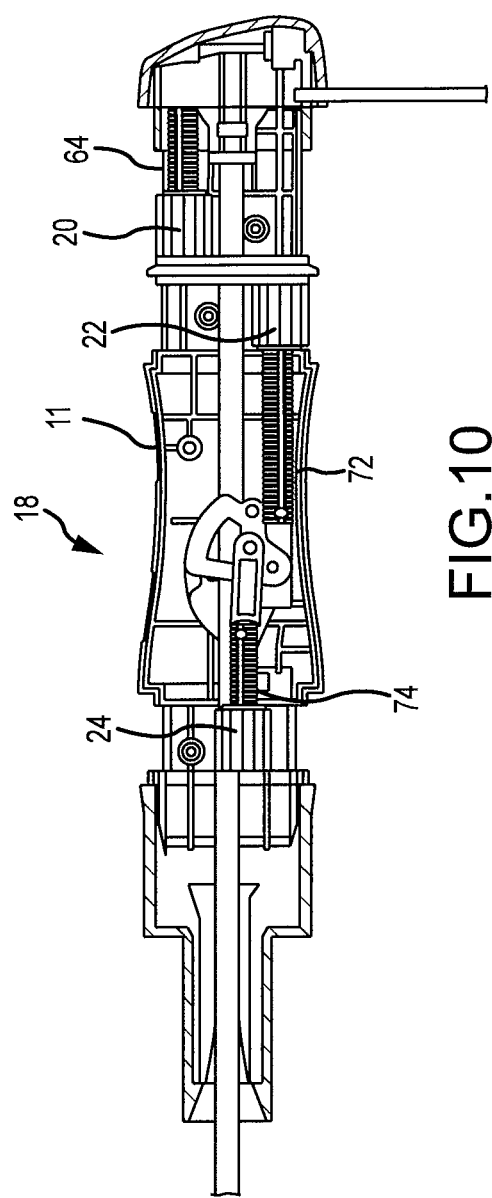
FIG. 10 is a cross-sectional view of the handle assembly depicted in FIG. 1, shown along line 10-10.
Figure 11:
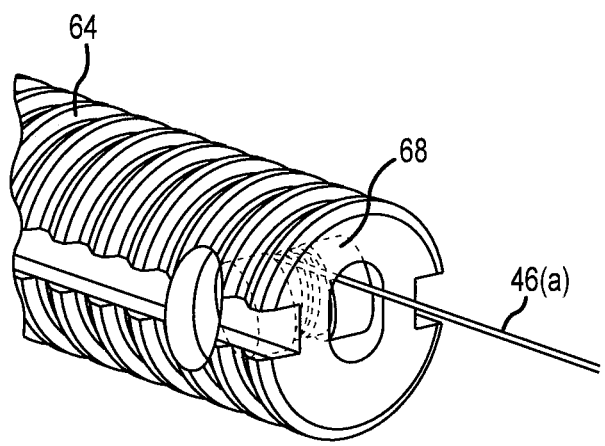
FIGS. 11-15 are views of components of the handle assembly depicted in FIG. 10, including an example of a guitar peg serving as a pull wire anchor.
Figure 12:
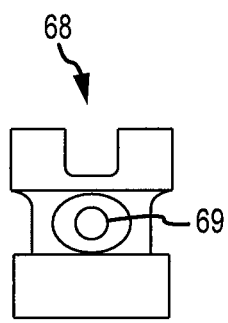

Referring to FIG. 10, a cross-sectional view of handle assembly 18 is shown (see also FIG. 1). A tension stud 64, articulation stud 72, and side steering stud 74 can be operably attached to tension knob 20, articulation knob 22, and side steering knob 24, respectively. Tension pull wire 46(*a*), retroflex pull wire 46(*d*), and right side steering pull 46(*c*) (not shown) are threaded through and around studs 64, 72, and 74, respectively. Left side steering wire 46(*b*) is threaded through a stud similar to stud 74 on the opposite side of handle assembly 18 (not shown). Accordingly, articulation of one or more of knobs 20, 22, 24 can move one or more of studs 64, 72, 74, respectively, with respect to handle body 11 and thereby effectuate steering, deflecting, bending, and/or articulation of steerable distal tip section 17.

Figure 13:
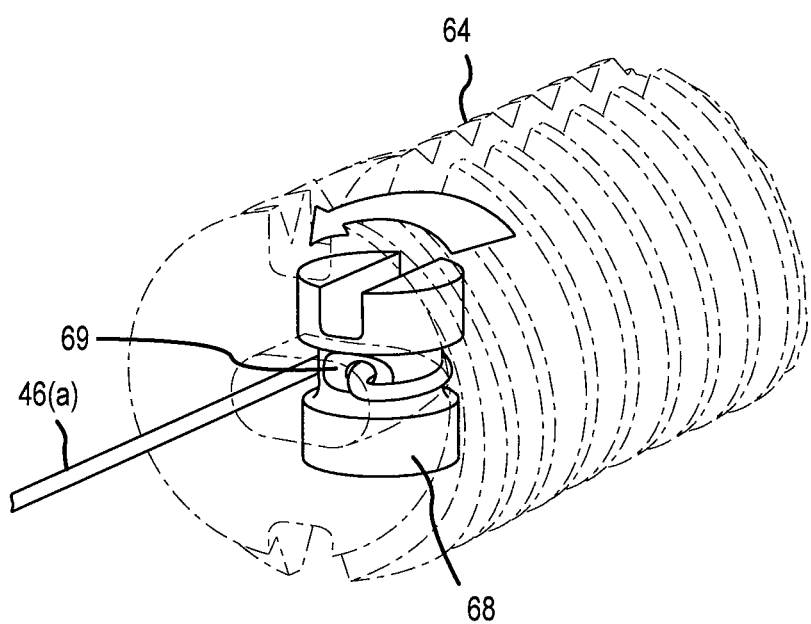
Figure 14:
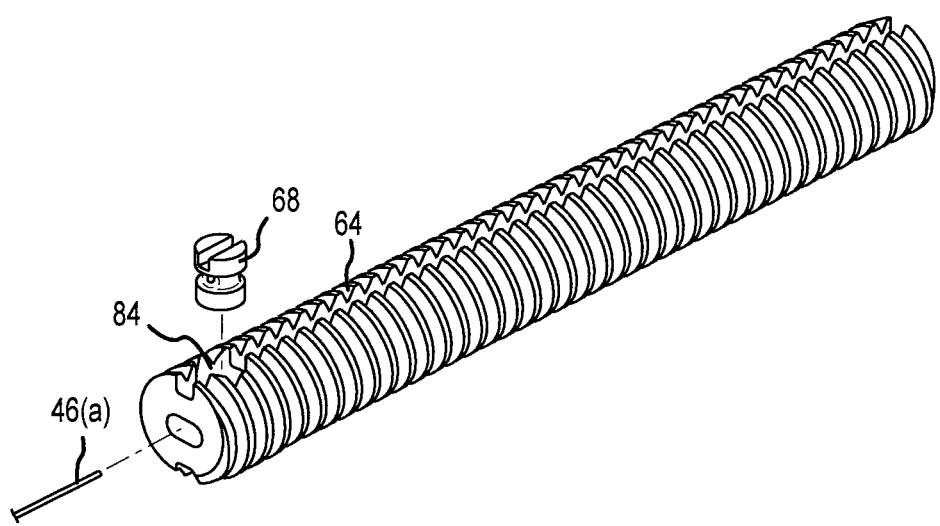
Figure 15:
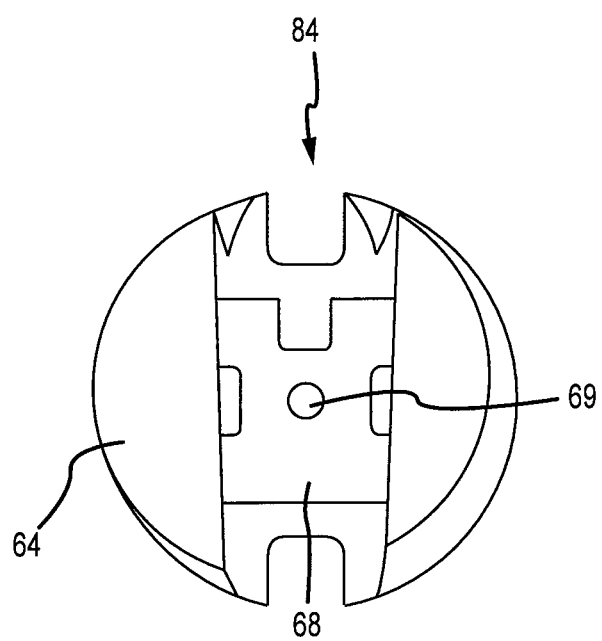

Referring to FIGS. 11-15, a portion of handle assembly 18 is shown in greater detail. A threaded rod, such as tension stud 64, can be operably connected to an operational knob, such as tension knob 20 (see FIG. 10), for example. Guitar peg 68, positioned within stud 64, serves as a wire anchor. Tension pull wire 46(*a*) can be anchored via hole 69 and wrapped around guitar peg 68 for two to three full turns, for example, as shown in FIG. 13. Since the diameter of the guitar peg 68 is much larger than the diameter of tension pull wire 46(*a*), less stress is placed on tension pull wire 46(*a*) when it is wrapped around the guitar peg 68, as there are no stress concentrations caused by tight diameter bends and/or kinking. Furthermore, guitar peg 68 can allow for fine tuning of tension pull wire 46(*a*), as well as maintenance of ultimate tensile strength of tension pull wire 46(*a*) for maximum performance. In an example, guitar peg 68 can be tapered to a specific angle. A hole 84 in tension stud 64 or another stud can likewise be tapered to the same specific angle, as shown in FIGS. 14-15. When a tapered guitar peg 68 is placed in the tapered hole 84, it is locked in place by friction. This locking further secures and strengthens the anchored pull wire.

In various embodiments, a deflectable introducer, such as steerable introducer 10, may be used to deliver a medical device to a target location in a patient's body. For example, after/during insertion of the introducer into the heart or other portion of the cardiovascular system, the side steering knob could be manipulated to steer the steerable section 'left' or 'right' to a desired location. Then, the articulation knob may be adjusted to deflect a portion of the steerable section into a desired angle for the delivery of a medical device, while the tension knob may be simultaneously or thereafter actuated to maintain a stable shaft position. Such a medical device could include an implantable medical device, such as a catheter, a heart valve, a heart valve repair device, etc. An exemplary repair device may include a mitral valve repair device such as that shown and described in U.S. patent application No. 61/902,964, referenced above.

Although embodiments of an articulation support member for a deflectable introducer have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the devices. Joinder references (e.g., affixed, attached, coupled, connected, and the like) are to be construed broadly and can include intermediate members between a connection of elements and relative movement between elements. As such, joinder references do not necessarily infer that two elements are directly connected and in fixed relationship to each other. It is intended that all matter contained in the above description or shown in the accompanying drawings shall be interpreted as illustrative only and not limiting. Changes in detail or structure can be made without departing from the spirit of the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Various embodiments have been described above to various apparatuses, systems, and/or methods. Numerous specific details have been set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated above are non-limiting examples, and thus it can be appreciated that the specific structural and functional details disclosed above may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

It will be appreciated that the terms "proximal" and "distal" have been used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" have been used above with respect to the illustrated embodiments. However, surgical instruments may be used in many orientations and positions, and these terms are not intended to be limiting and absolute.

What is claimed is:

1. A steerable introducer comprising
a shaft with a proximal end portion, a distal end portion, and a shaft longitudinal axis extending between the proximal end portion and the distal end portion;
a steerable distal tip section attached to the distal end portion of the shaft, the steerable distal tip section comprising an articulation support member;
a retroflex pull wire extending from the proximal end portion of the shaft to the distal end portion of the shaft, wherein the retroflex pull wire is anchored at a first anchor position on a distal pull ring portion of the articulation support member, the first anchor position being laterally offset from the shaft longitudinal axis in a first direction;
at least one tension pull wire extending from the proximal end portion of the shaft to the distal end portion of the shaft, wherein the at least one tension pull wire is anchored at a second anchor position on a proximal pull ring portion of the articulation support member, the second anchor position being (i) laterally offset from the shaft longitudinal axis in a second direction and (ii) angularly offset from the distal pull ring portion by a first angle, wherein the first direction is different from the second direction, and wherein the first angle is about 180 degrees; and
a handle assembly operably attached to the shaft, the handle assembly comprising at least one stud;
wherein tension on the retroflex pull wire causes the steerable distal tip section to bend in the first direction;
wherein the tension on the tension pull wire opposes shaft bending in the first direction; and
wherein one of the retroflex pull wire or the tension pull wire is anchored to a guitar peg connection, the guitar peg connection located within the at lease one stud and operably connected to the stud.

2. The steerable introducer of claim 1, wherein the retroflex pull wire causes the shaft to bend between about 0-120 degrees in the first direction.

3. The steerable introducer of claim 1, wherein the tension pull wire causes the shaft to bend between about 0-20 degrees in the second direction.

4. The steerable introducer of claim 1, wherein a cross-sectional area of a lumen of the shaft is maintained during bending.

5. The steerable introducer of claim 1 wherein the guitar peg connection is tapered to a specific angle; wherein a hole within the stud is tapered to the specific angle; and wherein the guitar peg is configured to lock into the hole.

6. The steerable introducer of claim 5, wherein the guitar peg connection is configured to lock into the hole via friction.

7. The steerable introducer of claim 1, wherein the one of the retro flex pull wire or the tension pull wire is configured to wrap around the guitar peg connection for at least one full turn.

8. The steerable introducer of claim 1, wherein the guitar peg connection allows maintenance of a full tensile strength of the one of the retro flex pull wire or the tension pull wire.

9. The steerable introducer of claim 1, wherein the one of the retro flex pull wire or the tension pull wire is anchored to the guitar peg connection via a hole extending through a central portion of the guitar peg connection.

10. The steerable introducer of claim 1, wherein a diameter of the guitar peg connection is larger than a diameter of the one of the retro flex pull wire or the tension pull wire.

11. A steerable introducer comprising
a shaft with a proximal end portion, a distal end portion, and a shaft longitudinal axis extending between the proximal end portion and the distal end portion;
a steerable distal tip section attached to the distal end portion of the shaft, the steerable distal tip section comprising an articulation support member;
a first pull wire extending from the proximal end portion of the shaft to the distal end portion of the shaft, wherein the first pull wire is anchored at a first anchor position on the articulation support member, the first anchor position being laterally offset from the shaft longitudinal axis in a first direction;
a second pull wire extending from the proximal end portion of the shaft to the distal end portion of the shaft, wherein the second pull wire is anchored at a second anchor position on the articulation support member, the second anchor position being (i) laterally offset from the shaft longitudinal axis in a second direction and (ii) angularly offset from the first anchor position by a specified angle, wherein the first direction is different from the second direction; and
a handle assembly operably attached to the shaft, the handle assembly comprising at least one stud;
wherein tension on the first pull wire causes the shaft to bend in the first direction;
wherein the tension on the second pull wire causes the shaft to bend in the second direction; and
wherein one of the first pull wire or the second pull wire is anchored to a guitar peg connection, the guitar peg connection located within the at lease one stud and operably connected to the stud.

12. The steerable introducer of claim 11, wherein the specified angle is about 90 degrees and wherein the first direction is perpendicular to the second direction.

13. The steerable introducer of claim 11, wherein a cross-sectional area of a lumen of the shaft is maintained during bending.

14. The steerable introducer of claim 11, further comprising a third pull wire and a fourth pull wire;
wherein the third pull wire extends from the proximal end portion of the shaft to the distal end portion of the shaft and is anchored at a third anchor position on the articulation support member, the third anchor position being (i) laterally offset from the shaft longitudinal axis in a third direction and (ii) angularly offset from the first anchor position by about 90 degrees;
wherein the fourth pull wire extends from the proximal end portion of the shaft to the distal end portion of the shaft and is anchored at a fourth anchor position on the articulation support member, the fourth anchor position being (i) laterally offset from the shaft longitudinal axis in a fourth direction and (ii) angularly offset from the second anchor position by about 90 degrees;
wherein tension on the third pull wire causes the shaft to bend in the third direction; and
wherein the tension on the fourth pull wire causes the shaft to bend in the fourth direction.

15. The steerable introducer of claim 14, wherein the third anchor position is longitudinally offset from the fourth anchor position; wherein the first anchor position is longitudinally offset from the third anchor position and the fourth anchor position; and wherein the second anchor position is longitudinally offset from the first anchor position and the fourth anchor position.

16. The steerable introducer of claim 14, wherein the articulation support member comprises a first region and a second region; wherein the first region defines a first bending plane; wherein the second region defines a second bending plane; and wherein the first bending plane is perpendicular to the second bending plane.

17. The steerable introducer of claim 11 wherein the guitar peg connection is tapered to a specific angle; wherein a hole within the stud is tapered to the specific angle;
and wherein the guitar peg is configured to lock into the hole.

18. The steerable introducer of claim 17, wherein the guitar peg connection is configured to lock into the hole via friction.

19. The steerable introducer of claim 11, wherein the one of the first pull wire or the second pull wire is configured to wrap around the guitar peg connection for at least one full turn.

20. The steerable introducer of claim 11, wherein the guitar peg connection allows maintenance of a full tensile strength of the one of the first pull wire or the second pull wire.

* * * * *